(12) United States Patent
Dun et al.

(10) Patent No.: US 12,201,533 B2
(45) Date of Patent: Jan. 21, 2025

(54) TECHNOLOGIES FOR DETERMINING SEATING OF AN ORTHOPAEDIC IMPLANT DURING AN ORTHOPAEDIC SURGICAL PROCEDURE

(71) Applicant: DEPUY SYNTHES PRODUCTS, INC., Raynham, MA (US)

(72) Inventors: Shouchen Dun, Fort Wayne, IN (US); Dustin R. Whitaker, Akron, IN (US); Michael T. Saloka, Mt. Zion, IL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 162 days.

(21) Appl. No.: 18/107,256

(22) Filed: Feb. 8, 2023

(65) Prior Publication Data

US 2023/0181336 A1 Jun. 15, 2023

Related U.S. Application Data

(62) Division of application No. 16/685,133, filed on Nov. 15, 2019, now Pat. No. 11,596,528.

(51) Int. Cl.
*A61F 2/46* (2006.01)
*A61B 17/92* (2006.01)
*A61B 5/00* (2006.01)

(52) U.S. Cl.
CPC ............ *A61F 2/4603* (2013.01); *A61B 17/92* (2013.01); *A61B 5/7405* (2013.01); *A61B 5/742* (2013.01); *A61B 5/7455* (2013.01); *A61B 2560/0266* (2013.01); *A61B 2560/0462* (2013.01)

(58) Field of Classification Search
CPC ........ A61F 2/46; A61F 2/4603; A61F 2/4609; A61B 17/92; A61B 5/742; A61B 5/7405; A61B 5/7455
See application file for complete search history.

(56) References Cited

U.S. PATENT DOCUMENTS

| 8,236,005 B2 | 8/2012 | Meneghini et al. |
| 2015/0282856 A1 | 10/2015 | Haiat et al. |
| 2017/0367847 A1 | 12/2017 | Piriou et al. |
| 2018/0116821 A1 | 5/2018 | Johannaber et al. |

(Continued)

FOREIGN PATENT DOCUMENTS

WO 2019/014537 A1 7/2019

OTHER PUBLICATIONS

Abou-Trabi D. et al., "Monitoring Femoral Component Insertion During Uncemented Total Hip Arthroplasty," Proceedings of the 24th International Modal Analysis Conference (IMAC), St. Louis, MO, Jan. 2006.

(Continued)

*Primary Examiner* — Christopher J Beccia
(74) *Attorney, Agent, or Firm* — Barnes & Thornburg LLP

(57) ABSTRACT

Technologies for determining seating of an orthopaedic implant during an orthopaedic surgical procedure includes an impaction sensor and an impaction analyzer. The impaction sensor produces sensor data, in response to an impaction between an orthopaedic mallet and a surgical tool indicative of an initial impact and a secondary impact of the impaction. The impaction analyzer analyzes the sensor data to determine a temporal length between the initial and secondary impacts and determines whether the orthopaedic implant is sufficiently seated into the bone based on the temporal length.

12 Claims, 13 Drawing Sheets

(56) References Cited

U.S. PATENT DOCUMENTS

2019/0125293 A1    5/2019  Behzadi
2021/0145603 A1    5/2021  Dun et al.

OTHER PUBLICATIONS

Crisman A. et al., "Femoral Component Insertion Monitoring Using Human Cadaveric Specimens," Proceedings of the 25th IMAC Conference on Structural Dynamics, Orlando, FL, Jan. 2007.
International Search Report and Written Opinion of the International Searching Authority for Application No. PCT/IB2020/059325, dated Jan. 20, 2021, 7 pages.

US 12,201,533 B2

TECHNOLOGIES FOR DETERMINING SEATING OF AN ORTHOPAEDIC IMPLANT DURING AN ORTHOPAEDIC SURGICAL PROCEDURE

CROSS-REFERENCE TO RELATED APPLICATION

The present application is a divisional of, and claims priority to, U.S. patent application Ser. No. 16/685,133, which was filed on Nov. 15, 2019, the entirety of which is hereby incorporated by reference.

TECHNICAL FIELD

The present disclosure relates generally to orthopaedic surgical tools and systems and, more particularly, to technologies for determining seating of an orthopaedic implant during an orthopaedic surgical procedure.

BACKGROUND

Joint arthroplasty is a well-known surgical procedure by which a diseased and/or damaged natural joint is replaced by a prosthetic joint, which may include one or more orthopaedic implants. For example, in a hip arthroplasty surgical procedure, a patient's natural hip ball and socket joint is partially or totally replaced by a prosthetic hip joint. Similarly, in a knee arthroplasty surgical procedure, a patient's natural knee joint is partially or totally replaced by a prosthetic knee joint.

One type of orthopaedic implants that may be used to replace a patient's joint are known as cementless orthopaedic implants. Cementless implants are implanted into a patient's boney anatomy by impacting the implant into a corresponding bone of the patient. For example, a cementless acetabular prosthesis typically includes an acetabular cup outer shell, which is configured to be implanted into a patient's acetabulum. To do so, an orthopaedic surgeon impacts the outer shell into the patient's acetabulum until the outer shell is sufficiently seated into the patient's surrounding bony anatomy. Similarly, in other arthroplasty surgical procedures such as knee arthroplasty surgical procedures, an orthopaedic surgeon strives for proper seating of the corresponding orthopaedic implant.

Typically, orthopaedic surgeons rely on experience and tactile and auditory feedback during the surgical procedure to determine when the orthopaedic implant is sufficiently impacted or seated into the patient's boney anatomy. For example, the surgeon may rely on tactile sensations felt through an impactor or inserter tool while the surgeon hammers the surgical tool with an orthopaedic mallet to impact the implant into the patient's boney anatomy. However, solely relying on such environmental feedback can result in the under or over impaction of the orthopaedic implant into the patient's bone. Over impaction can result in fracture of the patient's corresponding bone, while under impaction can result in early loosening of the orthopaedic implant.

SUMMARY

According to one aspect, the present disclosure includes an orthopaedic mallet for use in an orthopaedic surgical procedure to implant an orthopaedic implant into a bone of a patient. The orthopaedic mallet includes an impaction sensor and an impaction analyzer. The impaction sensor is configured to produce sensor data indicative of an impaction of the orthopaedic mallet and a surgical tool. The impaction includes an initial impact between the orthopaedic mallet and the surgical tool and a secondary impact between the orthopaedic mallet and the surgical tool that occurs subsequent to the initial impact. The impaction analyzer is configured to analyze the sensor data to detect the initial impact and the secondary impact, determine a temporal length between the initial impact and the secondary impact, and determine whether the orthopaedic implant is sufficiently seated into the bone based on the temporal length.

In an embodiment, the impaction analyzer may detect the initial impact and the secondary impact in response to a determination that a value of the sensor data is greater than a reference threshold. In some embodiments, the impaction analyzer may determine that the orthopaedic implant is sufficiently seated in response to a determination that the temporal length between the initial impact and the secondary impact is less than a reference threshold. Alternatively, in some embodiments, the impaction analyzer may determine that the orthopaedic implant is sufficiently seated in response to a determination that a difference between the temporal length and a prior temporal length of a prior initial impact and a corresponding prior secondary impact is less than a reference threshold. For example, in some embodiments, the impaction defines a second impaction and the temporal length defines a second temporal length. In such embodiments, the impaction sensor may be configured to produce additional sensor data indicative of a first impaction of the orthopaedic mallet and the surgical tool that occurred prior to the second impaction, wherein the first impaction comprises an initial impact between the orthopaedic mallet and the surgical tool and a secondary impact between the orthopaedic mallet and the surgical tool that occurs subsequent to the initial impact of the first impaction. Additionally, the impaction analyzer may be configured to analyze the additional sensor data to detect the initial impact of the first impaction and the secondary impact of the first impaction, determine a first temporal length between the initial impact of the first impaction and the secondary impact of the first impaction, and determine that the orthopaedic implant is sufficiently seated in response to a determination that a difference between the first temporal length and the second temporal length is less than a referenced amount.

In some embodiments, the orthopaedic mallet may further include and output device, and the impaction analyzer may be configured to activate the output device in response to a determination that the orthopaedic implant is sufficiently seated into the bone to alert a user of the orthopaedic mallet. For example, the orthopaedic mallet may include a plurality of output devices, and the impaction analyzer may be configured to determine which one of the plurality of output devices to activate as a function of the temporal length. The output devices may be embodied as, or otherwise include, a visual output device, an audible output device, or a tactile output device. Additionally, the impaction sensor may be embodied as, or otherwise include, a force sensor, a strain gauge, or an audio sensor.

According to another aspect, the present disclosure includes a system for determining whether an orthopaedic implant is sufficiently seated in a bone of a patient during an orthopaedic surgical procedure, the system comprising. The system includes an impaction sensor and an impaction analyzer. The impaction sensor is configured to produce sensor data indicative of an impaction of the orthopaedic mallet and a surgical tool. The impaction includes an initial impact between the orthopaedic mallet and the surgical tool and a secondary impact between the orthopaedic mallet and the surgical tool that occurs subsequent to the initial impact. The impaction analyzer is configured to analyze the sensor data to detect the initial impact and the secondary impact, determine a temporal length between the initial impact and the secondary impact, and determine whether the orthopaedic implant is sufficiently seated into the bone based on the temporal length.

In some embodiments, the impaction sensor may be located on the orthopaedic mallet, and the impaction analyzer may be embodied as a compute device separate from the orthopaedic mallet and the surgical tool. Alternatively, in some embodiments, the impaction sensor may be located on the surgical tool, and the impaction analyzer may be located on the orthopaedic mallet. In other embodiments, the impaction sensor may be located on the surgical tool, and the impaction analyzer may be embodied as a compute device separate from the orthopaedic mallet and the surgical tool. Alternatively, in some embodiments, the impaction sensor and the impaction analyzer are both separate from the orthopaedic mallet and the surgical tool.

In an embodiment, the impaction analyzer may detect the initial impact and the secondary impact in response to a determination that a value of the sensor data is greater than a reference threshold. In some embodiments, the impaction analyzer may determine that the orthopaedic implant is sufficiently seated in response to a determination that the temporal length between the initial impact and the secondary impact is less than a reference threshold. Alternatively, in some embodiments, the impaction analyzer may determine that the orthopaedic implant is sufficiently seated in response to a determination that a difference between the temporal length and a prior temporal length of a prior initial impact and a corresponding prior secondary impact is less than a reference threshold.

According to a further aspect, the present disclosure includes one or more non-transitory, machine-readable media comprising a plurality of instructions that, in response to execution, cause one or more processors to obtain, from an impaction sensor, sensor data indicative of an impaction of an orthopaedic mallet and a surgical tool, wherein the impaction comprises an initial impact between the orthopaedic mallet and the surgical tool and a secondary impact between the orthopaedic mallet and the surgical tool that occurs subsequent to the initial impact. Additionally, the instructions may cause the one or more processors to analyze the sensor data to detect the initial impact and the secondary impact, determine a temporal length between the initial impact and the secondary impact, and determine whether the orthopaedic implant is sufficiently seated into the bone based on the temporal length.

In an embodiment, the one or more processors may detect the initial impact and the secondary impact in response to a determination that a value of the sensor data is greater than a reference threshold. In some embodiments, the one or more processors may determine that the orthopaedic implant is sufficiently seated in response to a determination that the temporal length between the initial impact and the secondary impact is less than a reference threshold. Alternatively, in some embodiments, the one or more processors may determine that the orthopaedic implant is sufficiently seated in response to a determination that a difference between the temporal length and a prior temporal length of a prior initial impact and a corresponding prior secondary impact is less than a reference threshold. For example, in some embodiments, the impaction defines a second impaction and the temporal length defines a second temporal length. In such embodiments, the impaction sensor may be configured to produce additional sensor data indicative of a first impaction of the orthopaedic mallet and the surgical tool that occurred prior to the second impaction, wherein the first impaction comprises an initial impact between the orthopaedic mallet and the surgical tool and a secondary impact between the orthopaedic mallet and the surgical tool that occurs subsequent to the initial impact of the first impaction. Additionally, the one or more processors may be configured to analyze the additional sensor data to detect the initial impact of the first impaction and the secondary impact of the first impaction, determine a first temporal length between the initial impact of the first impaction and the secondary impact of the first impaction, and determine that the orthopaedic implant is sufficiently seated in response to a determination that a difference between the first temporal length and the second temporal length is less than a referenced amount.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
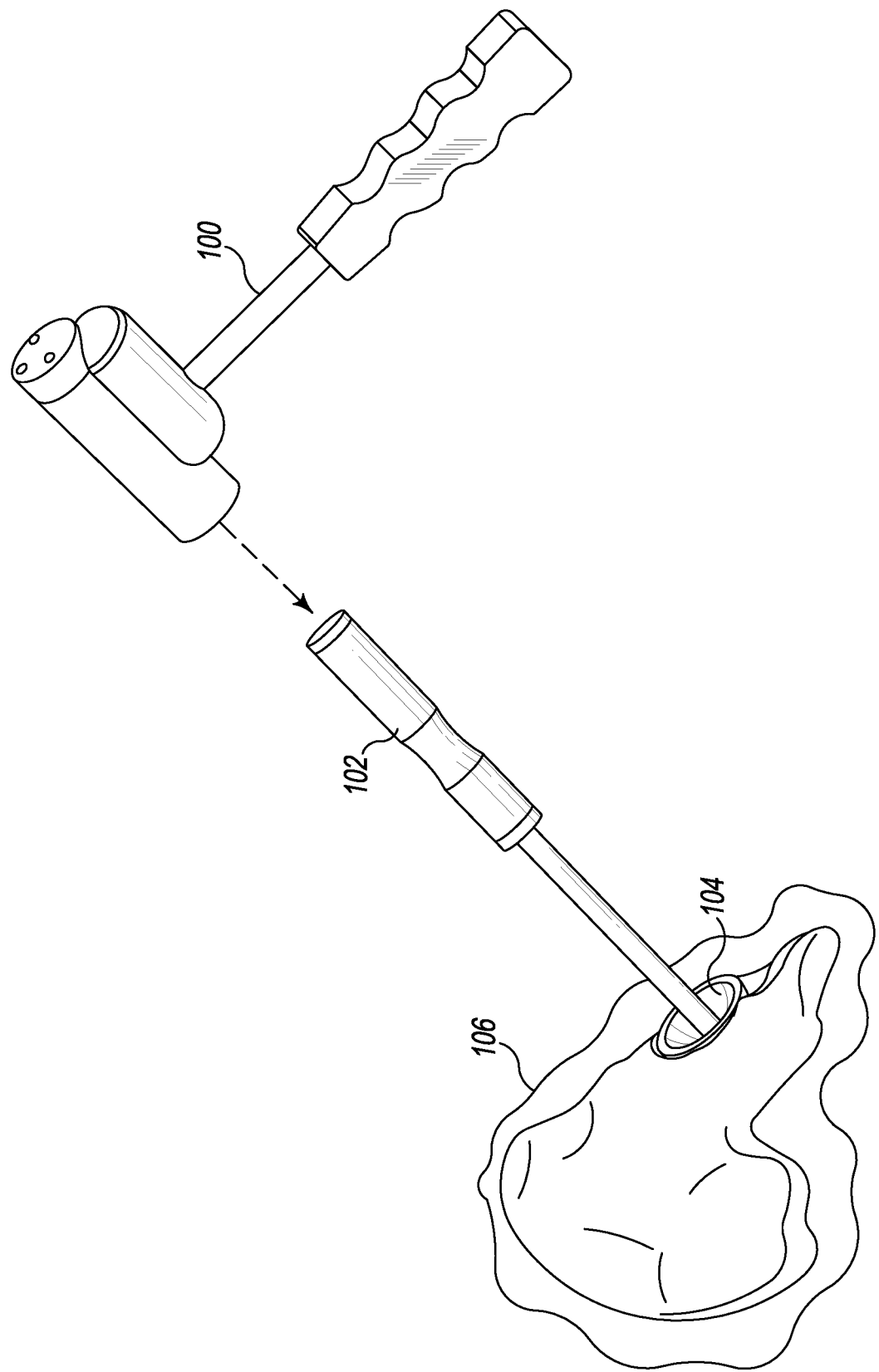
FIG. 1 is a perspective view of a "smart" orthopaedic mallet in use with a surgical tool to perform an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a "smart" orthopaedic mallet 100 is configured to produce sensor data indicative of an impaction between the orthopaedic mallet 100 and a surgical tool 102 and determine whether an orthopaedic implant 104 is properly or sufficiently seated in a bone 106 of a patient based on the received impaction sensor data. For example, during some associated orthopaedic procedures such as the hip arthroplasty surgical procedure illustrated shown in FIG. 1, an orthopaedic surgeon may be required to impact the orthopaedic implant 104 (e.g., a cementless acetabular cup shell) into the boney anatomy of the patient (e.g., the patient's acetabulum). To do so, the orthopaedic surgeon impacts or otherwise strikes the surgical tool 102, which may be embodied as an implant inserter or impactor, with the orthopaedic mallet 100. Typically, the implantation of the orthopedic implant into a patient's bone will require a series of strikes or impactions between the orthopaedic mallet 100 and the surgical tool 102.

It has been noted, however, that each individual impaction between the orthopaedic mallet 100 and the surgical tool 102 includes an initial or primary impact and a secondary impact (and, in many cases, further impacts), which occurs subsequently to the initial impact. The secondary impact is generally not intended by the orthopaedic surgeon, but occurs do to the physics of the impaction between the orthopaedic mallet 100 and the surgical tool 102.

Figure 2:
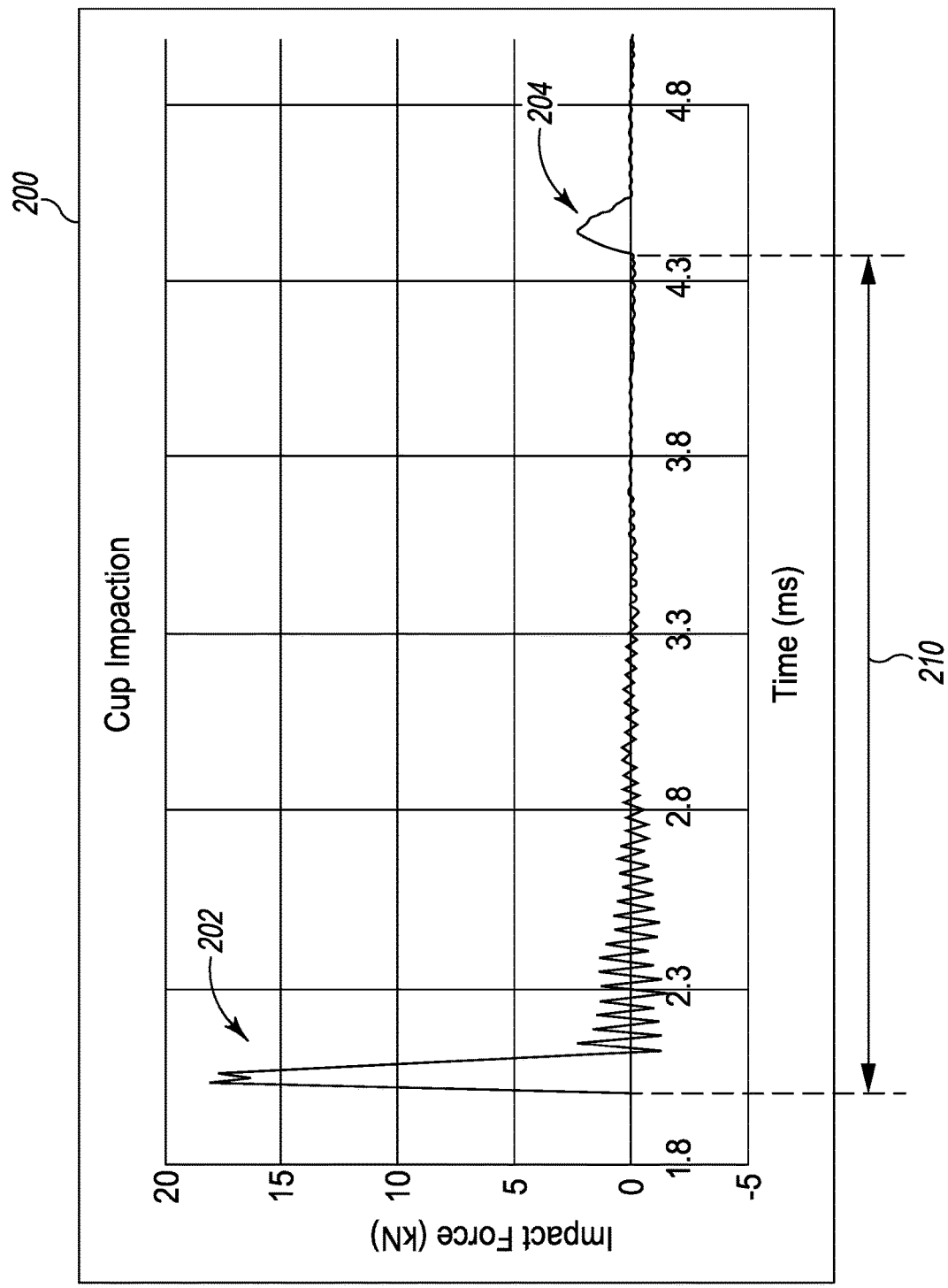
FIG. 2 is a graph illustrating impact force over time for an impaction between an orthopaedic mallet and a surgical tool, which includes an initial impact and a secondary impact.

For example, as shown in FIG. 2, a graph 200 illustrates multiple impacts between the orthopaedic mallet 100 and the surgical tool 102 that occur during a single impaction event (i.e., as a result of a single strike of the orthopaedic mallet 100 onto the surgical tool 102). As shown, the impaction includes an initial or primary impact 202, which has a large force magnitude as indicated by the ordinate axis of the graph 200. Additionally, the impaction includes a secondary impact 204, which has a moderate force magnitude less than the initial impact 202, but still noticeably distinct. It should be appreciated that the impaction of the orthopaedic mallet 100 and the surgical tool 102 illustrated in FIG. 2 is the result of an intended single strike (i.e., an impaction event) by the orthopaedic surgeon on the surgical tool 102 using the orthopaedic mallet 100, even though the single strike or impaction event actually includes multiple, distinct impacts or contact events between the orthopaedic mallet 100 and the surgical tool 102. That is, the secondary impact (and other resulting impacts) between by the orthopaedic mallet 100 and the surgical tool 102 may not be intended by the orthopedic surgeon, but occur nonetheless.

As shown in FIG. 2, the secondary impact 204 occurs sometime after the initial impact 202. That is, the secondary impact 204 is temporally separated from the initial impact 202 by a temporal length 210. It should be appreciated that the temporal length 210 changes as the orthopaedic implant 104 becomes seated into the patient's boney anatomy. In particular, the temporal length 210 between the initial impact 202 and the secondary impact 204 generally decreases as the associated orthopaedic implant 104 is implanted into the patient's bone 106.

Furthermore, in addition to the temporal length 210 decreasing as the orthopaedic implant 104 becomes seated into the patient's bone, the difference between temporal lengths 210 (i.e., the temporal distance between the initial impact 202 and the secondary impact 204 of a single strike or impaction event) of sequential strikes or impaction events decreases as the orthopaedic implant 104 becomes seated.

Figure 3:
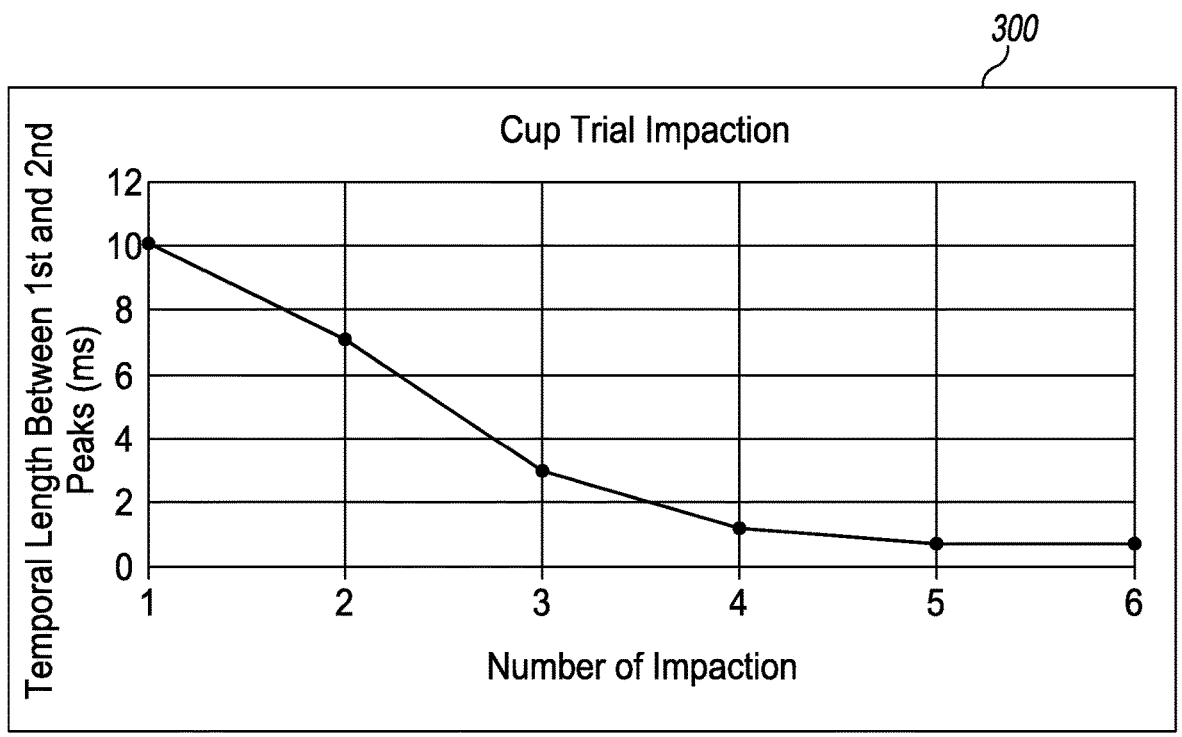
FIG. 3 is a graph illustrating a temporal length between an initial impact and a secondary impact of a series of impactions between an orthopaedic mallet and a surgical tool during implantation of an acetabular cup trail implant.
Figure 4:
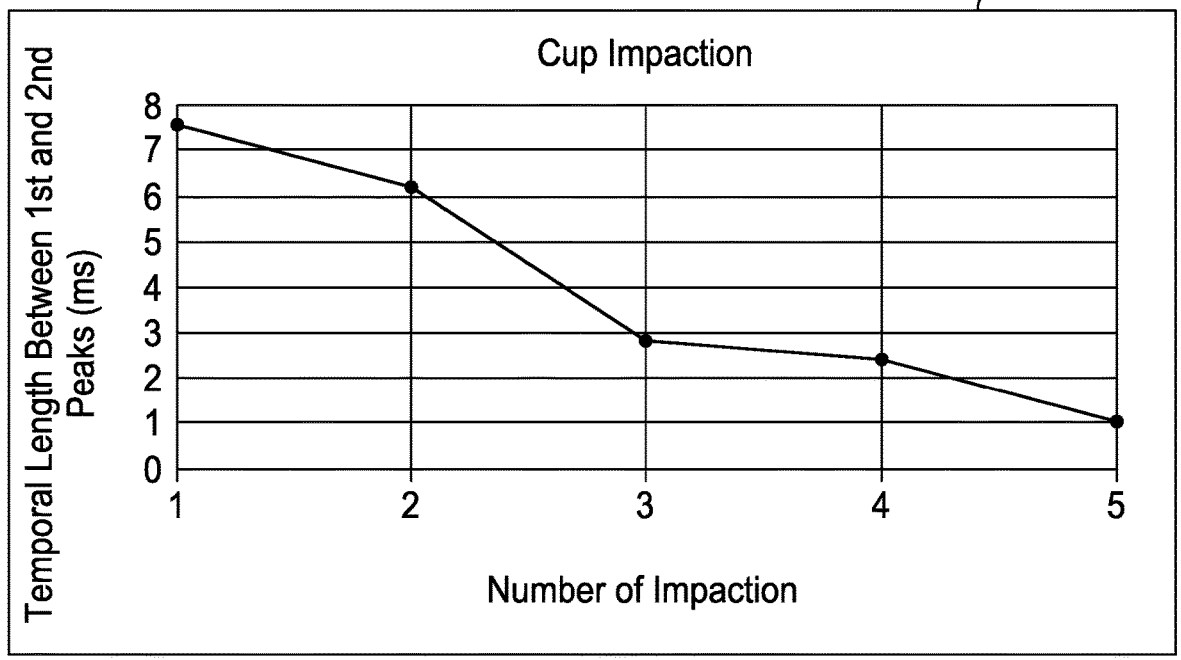
FIG. 4 is a graph illustrating a temporal length between an initial impact and a secondary impact of a series of impactions between an orthopaedic mallet and a surgical tool during implantation of an acetabular cup implant.

For example, as shown in FIG. 3, a graph 300 illustrates the difference in temporal lengths 210 of sequential impactions of the orthopaedic mallet 100 and the surgical tool 102 decreasing over time during implantation of an acetabular prosthetic cup trial. Similarly, as shown in FIG. 4, a graph 400 illustrates the difference in temporal lengths 210 of sequential impactions of the orthopaedic mallet 100 and the surgical tool 102 decreasing over time during implantation of an acetabular prosthetic cup. That is, the rate of change between temporal lengths 210 of sequential impaction events decreases over time, as the number of impaction events increases and the orthopaedic implant 104 becomes seated into the patient's bone 106. For example, the difference in temporal lengths between the first impaction/strike and the second impaction/strike is much greater than the difference in temporal lengths between the fourth impaction/strike and the fifth impaction/strike.

Figure 5:
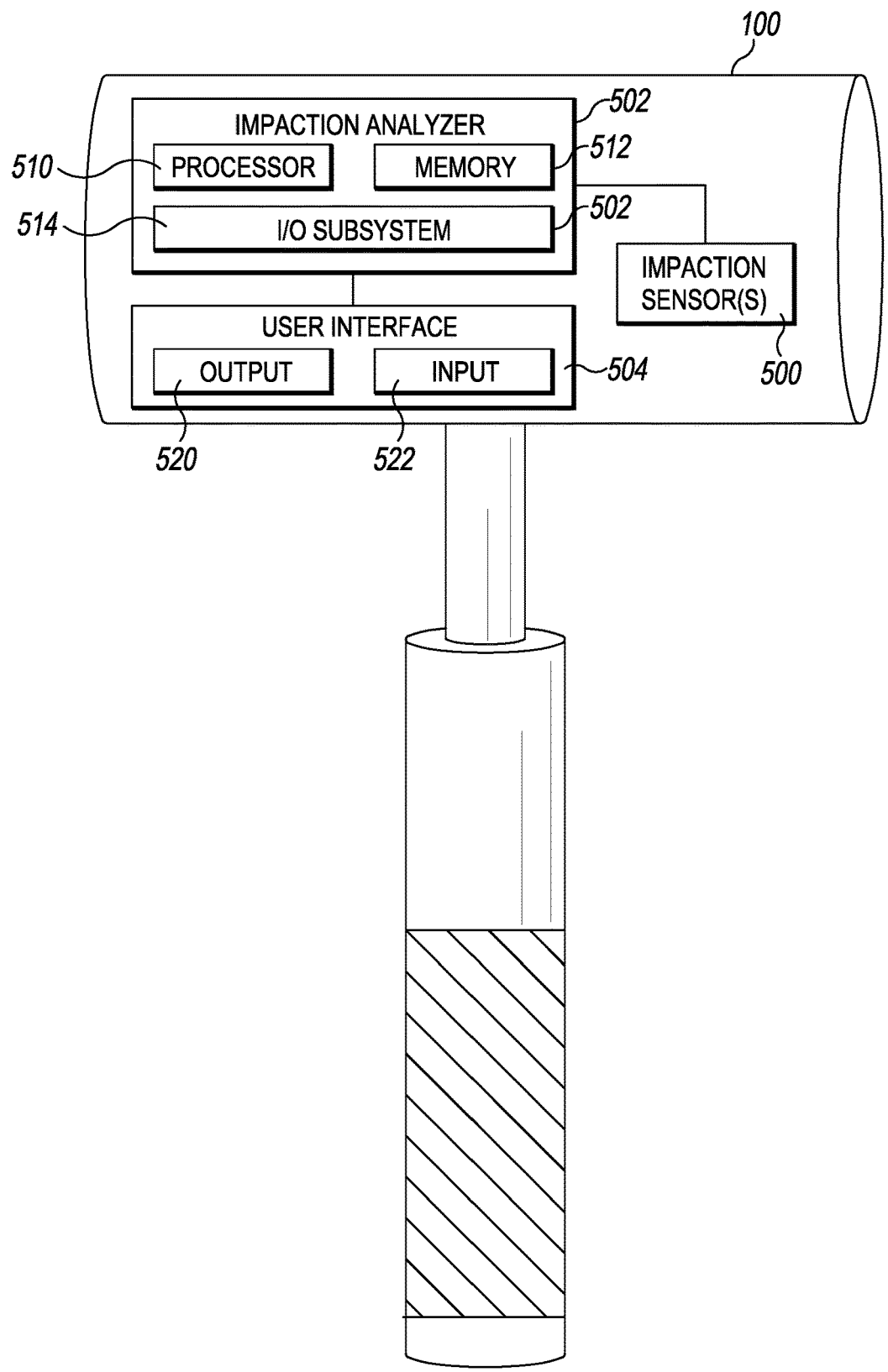
FIG. 5 is a schematic drawing of an embodiment of the orthopaedic mallet of FIG. 1 including an impaction analyzer for determining whether an orthopaedic implant is sufficiently seated in a bone of a patient during an orthopaedic surgical procedure.

As such, the orthopaedic mallet 100 is configured to determine whether the orthopaedic implant 104 is sufficiently or properly seated into the patient's bone 106 by analyzing the temporal length 210 between the initial impact 202 and the secondary impact 204 of an impaction event or by analyzing the difference in temporal lengths of sequential impaction events. To do so, as shown in FIG. 5, the illustrative orthopaedic mallet 100 includes one or more impaction sensors 500 and an impaction analyzer 502 configured to analyze impaction sensor data produced by the impaction sensor(s) 500. The orthopaedic mallet 100 also includes a user interface 504 to provide notifications to the orthopaedic surgeon or other user regarding the seating of the orthopaedic implant 104 during the performance of the associated orthopaedic surgical procedure.

In use, as discussed in more detail below, the impaction analyzer 502 analyzes the sensor data produced by the impaction sensor(s) 500 to detect the initial impact 202 and the secondary impact 204 for each impaction of the orthopaedic mallet 100. Additionally, the impaction analyzer 502 determines the temporal length 210 between the initial impact 202 and the secondary impact 204 for the associated impaction event and determines whether the orthopaedic implant 104 is sufficiently seated into the patient's bone based on the determined temporal length 210. For example in some embodiments, the impaction analyzer 502 may determine that the orthopaedic implant 104 is properly or sufficiently seated into the patient's bone 106 in response to a determination that the temporal length 210 is below a reference threshold value. In some embodiments, for example, the impaction analyzer 502 may determine that orthopaedic implant 104 is sufficiently seated when the temporal length 210 is 1 milliseconds or less. In other embodiments, the impaction analyzer 502 may determine that the orthopaedic implant 104 is properly or sufficiently seated into the patient's bone 106 in response to a determination that a difference between the temporal length 210 of an individual strike or impaction event of the mallet 100 and the temporal length 210 of an immediately prior individual strike or impaction event of the mallet 100 is less than a reference threshold value (i.e., that the rate of change of temporal lengths 210 of subsequent impactions is less than a reference threshold). For example, in particular embodiments, the impaction analyzer 502 may determine that orthopaedic implant 104 is sufficiently seated when the difference between sequential temporal lengths 210 is 0.2 milliseconds or less. Of course, other threshold reference values may be used in other embodiments depending on particular criteria, such as the orthopaedic implant being used, the particular orthopaedic surgical procedure being implemented, and/or the particular impactor/inserter being used.

The impactions sensor(s) 500 may be embodied as any type of sensor capable generating or producing sensor data indicative of a strike or impaction event between the orthopaedic mallet 100 and the surgical tool 102. In the illustrative embodiment, the impaction sensor 500 is embodied as a force sensor configured to generate force sensor data indicative of an impaction between the orthopaedic mallet 100 and the surgical tool 102. However, in other embodiments, the impaction sensor 500 may be embodied as a strain gauge, accelerometer, piezoelectric sensor, an audio sensor (e.g., a microphone), or other sensor capable of producing sensor data from which the impaction of the orthopaedic mallet 100 and the surgical tool 102 can be determined. Although only one impaction sensor 500 is shown in FIG. 5, it should be appreciated that the orthopaedic mallet 100 may include additional impaction sensors 500 in other embodiments. In such embodiments, the multiple impaction sensors 500 may be similar or of different types.

The impaction analyzer 502 may be embodied as any type of device or collection of devices capable of performing various compute functions and the functions described herein. In some embodiments, the impaction analyzer 502 may be embodied as a single device such as an integrated circuit, an embedded system, a field-programmable-array (FPGA), a system-on-a-chip (SOC), or other integrated system or device. In the illustrative embodiment, the impaction analyzer 502 includes a processor 510, a memory 512, and an input/output (IO) subsystem 514. The processor 510 may be embodied as any type of processor capable of performing the functions described herein. For example, the processor 510 may be embodied as a single or multi-core processor(s), a digital signal processor, a microcontroller, discrete compute circuitry, other processor or processing/controlling circuitry. Similarly, the memory 512 may be embodied as any type of volatile and/or non-volatile memory or data storage capable of storing data, such as the sensor data produced by the impaction sensor 500.

The impaction analyzer 502 is communicatively coupled to other components of the orthopaedic mallet 100 via the I/O subsystem 514, which may be embodied as circuitry and/or components to facilitate input/output operations with impaction analyzer 502 (e.g., with the processor 510 and/or memory 512) and other components of the orthopaedic mallet 100. For example, the I/O subsystem 514 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The user interface 504 may be embodied as a collection of various output and/or input devices to facilitate communication between the orthopaedic mallet 100 and a user. Illustratively, the user interface 504 includes one or more output devices 520 and/or one or more input devices 522. Each of the output devices 520 may be embodied as any type of output device capable of providing a notification or other information to the orthopaedic surgeon or other user. For example, the output devices 520 may be embodied as visual, audible, or tactile output devices. In the illustrative embodiment, the user interface 504 includes one or more visual output devices, such as a light emitting diode (LED), a light, a display screen, or the like. Each of the input devices 522 may be embodied as any type of input device capable of control or activation by the orthopedic surgeon to provide an input, data, or instruction to the impaction analyzer 502. For example, the input devices 522 may be embodied as a button (e.g., an on/off button), a switch, a touchscreen display, or the like.

Figure 6:
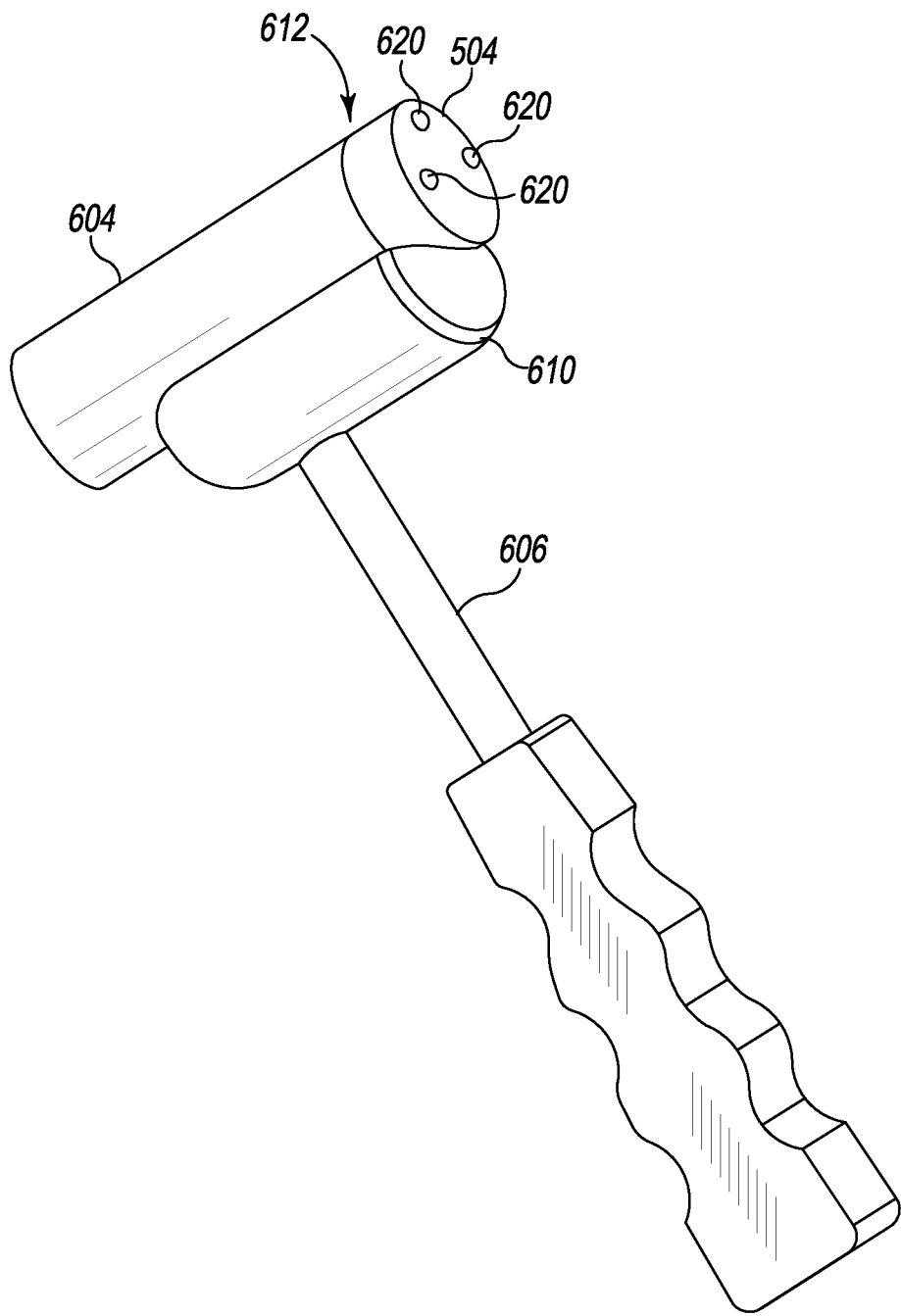
FIG. 6 is a perspective view of an embodiment of the orthopaedic mallet of FIG. 5.

Referring now to FIG. 6, an illustrative embodiment of the orthopaedic mallet 100 is shown. The illustrative mallet 100 includes a handle 602 and a mallet head 604 connected to the handle 602 via a shaft 606. As with a typical hammer or mallet, the orthopaedic surgeon may grasp the mallet 100 by the handle 602 and swing the mallet 100 to cause impaction of the mallet head 604 with the surgical tool 102 (or other structure). The illustrative orthopaedic mallet 100 also includes an enclosure 610 coupled to the mallet head 604, which houses the impaction analyzer 502. The impaction sensor(s) may also be housed in the enclosure 610 or be located elsewhere in the mallet head 604.

The mallet head 604 also includes the user interface 504 located on a backside 612 of the mallet head 604. The illustrative user interface 504 includes a set of LEDs 620. In user, as discussed in more detail below, the impaction analyzer 502 may be configured to activate or illuminate one of the LEDs 620 depending on how well the orthopaedic implant 104 is seated into the patient's bone 106. For example, the impaction analyzer 502 may illuminate a yellow LED (or other color) when the temporal length 210 of an impaction is above a first referenced threshold indicative that the orthopaedic implant 104 is not sufficiently seated, a green LED (or other color) when the temporal length 210 of an impaction is below the first reference threshold but above a second reference threshold indicative that the orthopaedic implant 104 is sufficiently seated (but not overly impacted), and a red LED (or other color) when the temporal length 210 of an impaction is below the second reference threshold indicative that the orthopaedic implant 104 is overly impacted and additional impacting may result in the fracturing of the patient's bone.

Figure 7:
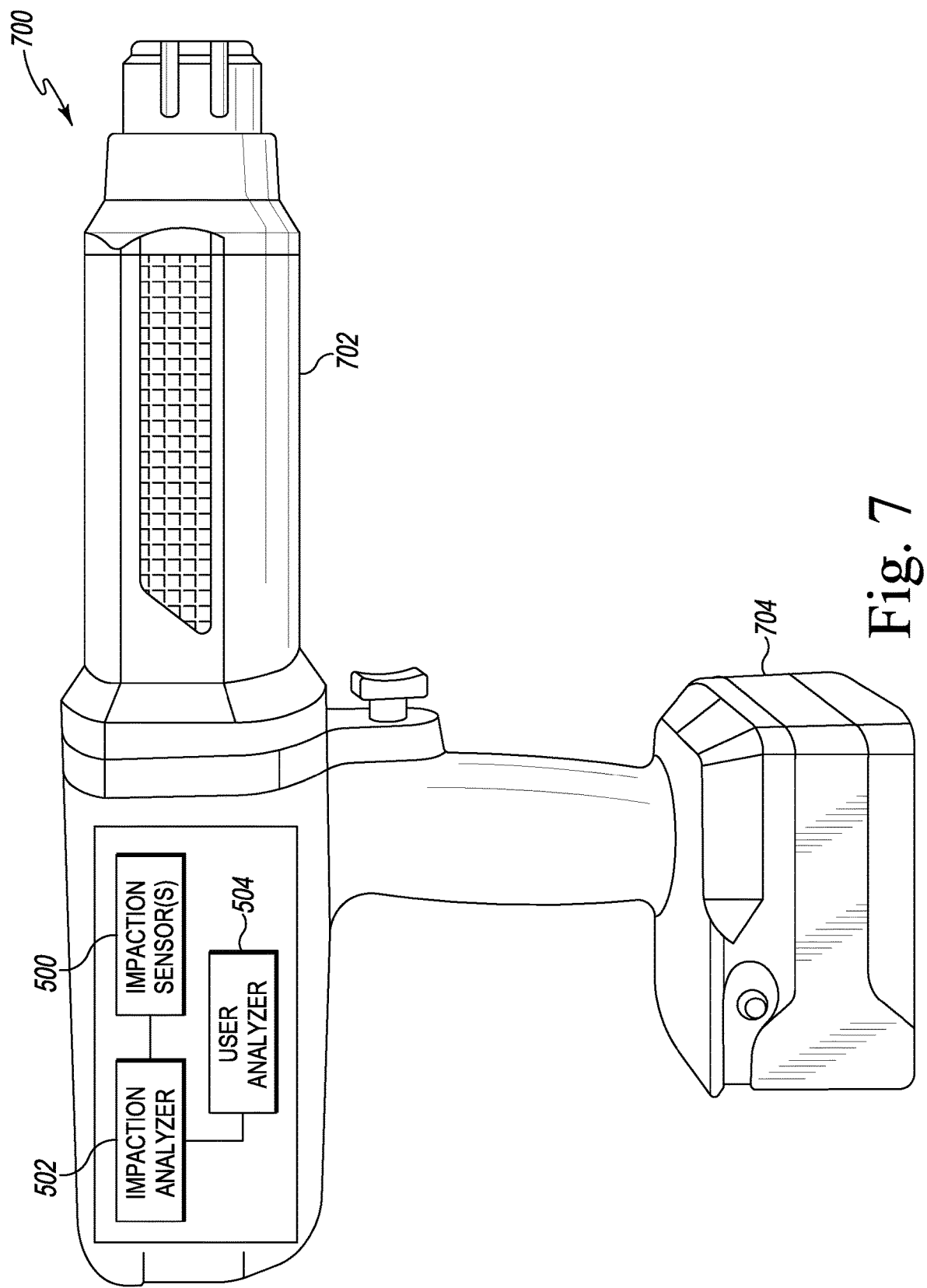
FIG. 7 is a schematic drawing of an embodiment of an automated orthopaedic impactor including the impaction analyzer of FIG. 5.

Referring now to FIG. 7, in some embodiments, the orthopaedic mallet 100 may be embodied as an automated impactor 700, rather than a manual mallet. For example, the automated impactor 700 may be embodied as a Kincise™ surgical automated system component commercially available from DePuy Synthes of Warsaw, Indiana In the illustrative embodiment, the automated impactor 700 includes a impactor body 702 and a battery pack 704, which provide power to electrical components located with the impactor body 702 configured to generate an impaction force. In such embodiments, the impaction sensor(s) 500, the impaction analyzer 502, and the user interface 504 may be located in or on the impactor body 702.

Figure 8:
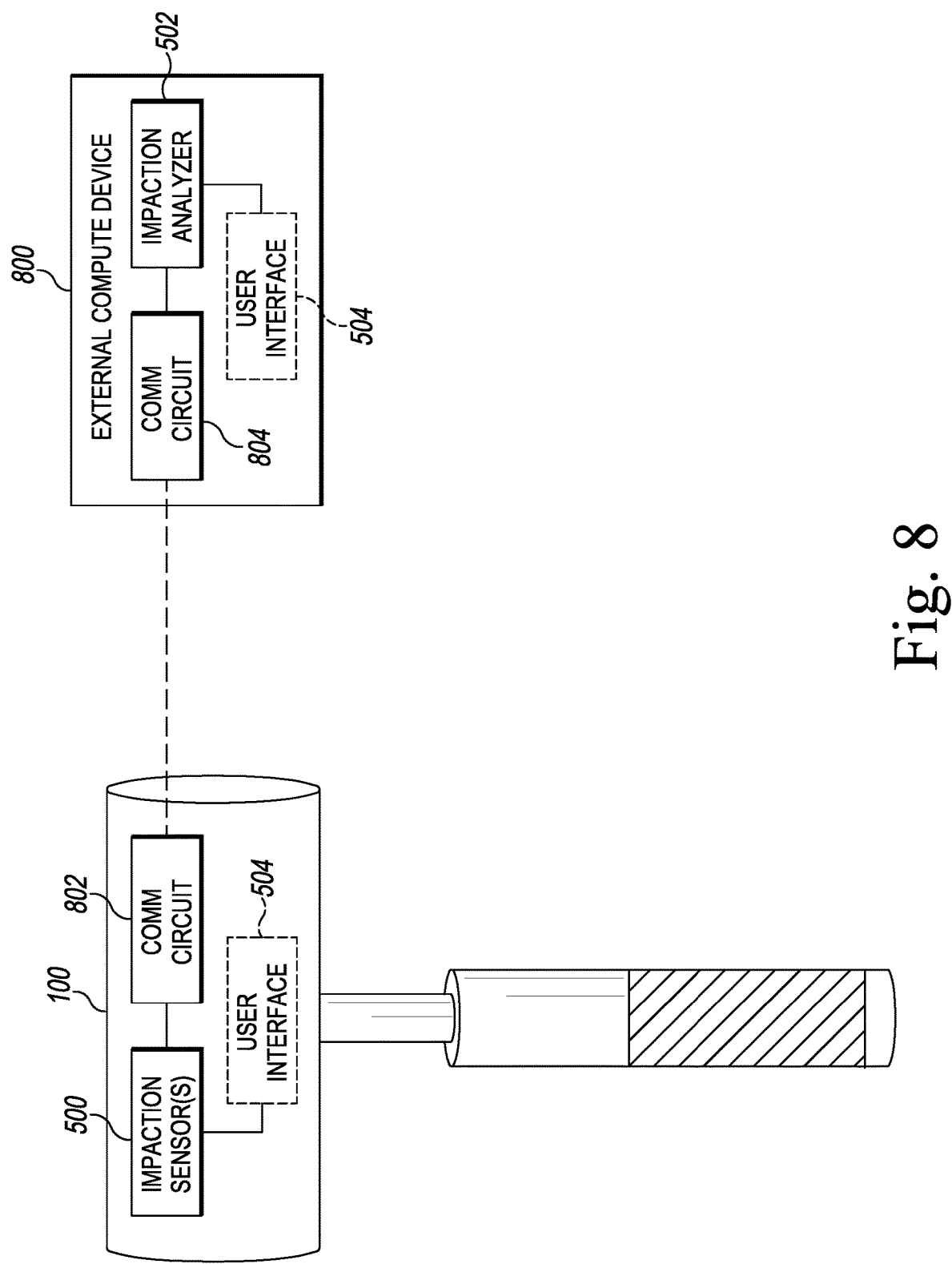
FIG. 8 is a schematic drawing of a system for determining whether an orthopaedic implant is sufficiently seated in a bone of a patient including an orthopaedic mallet and an external compute device including the impaction analyzer of FIG. 5.
Figure 9:
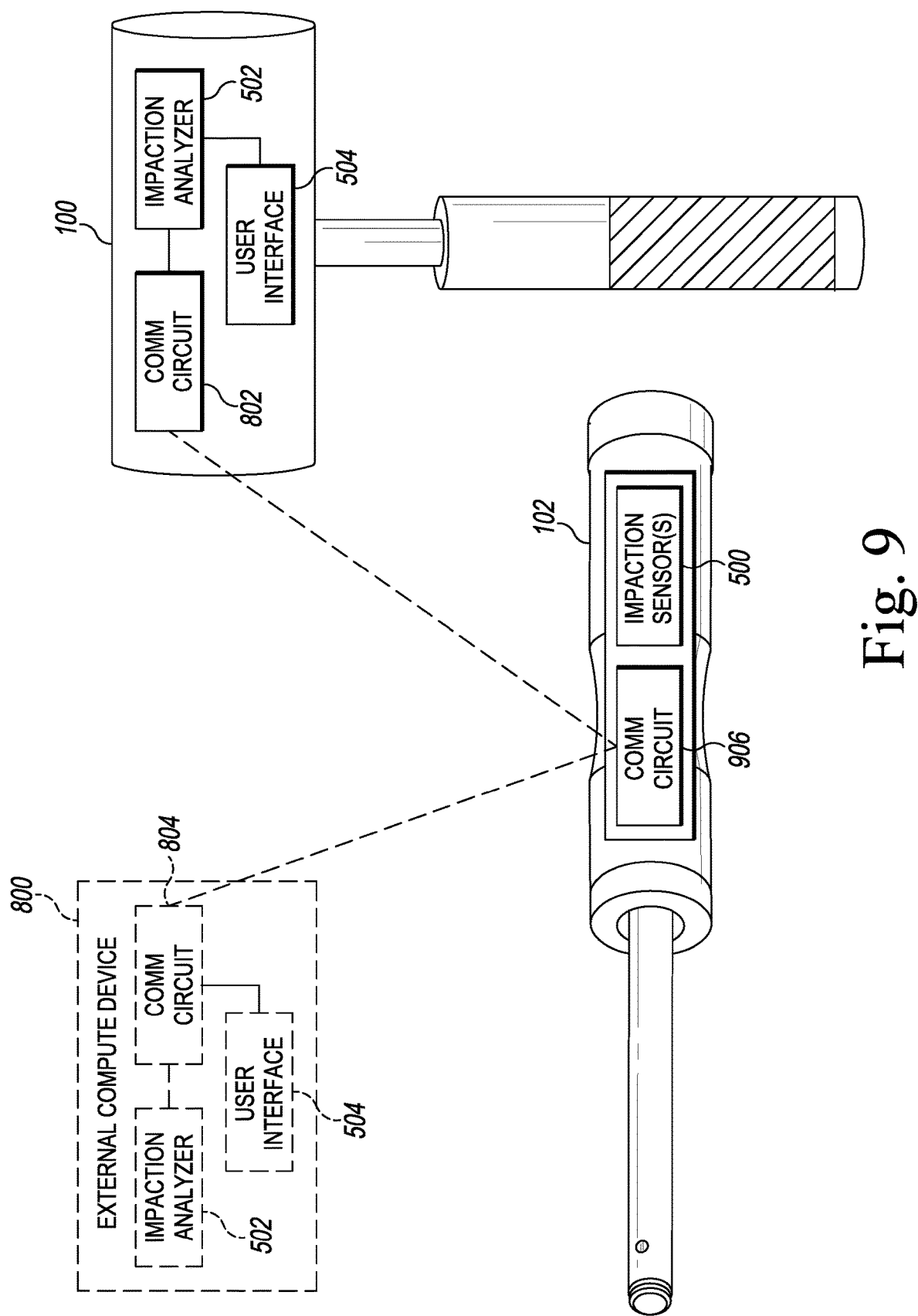
FIG. 9 is a schematic drawing of at least one additional embodiment of a system for determining whether an orthopaedic implant is sufficiently seated in a bone of a patient including an orthopaedic mallet, and orthopaedic tool, and, optionally, an external compute device.
Figure 10:
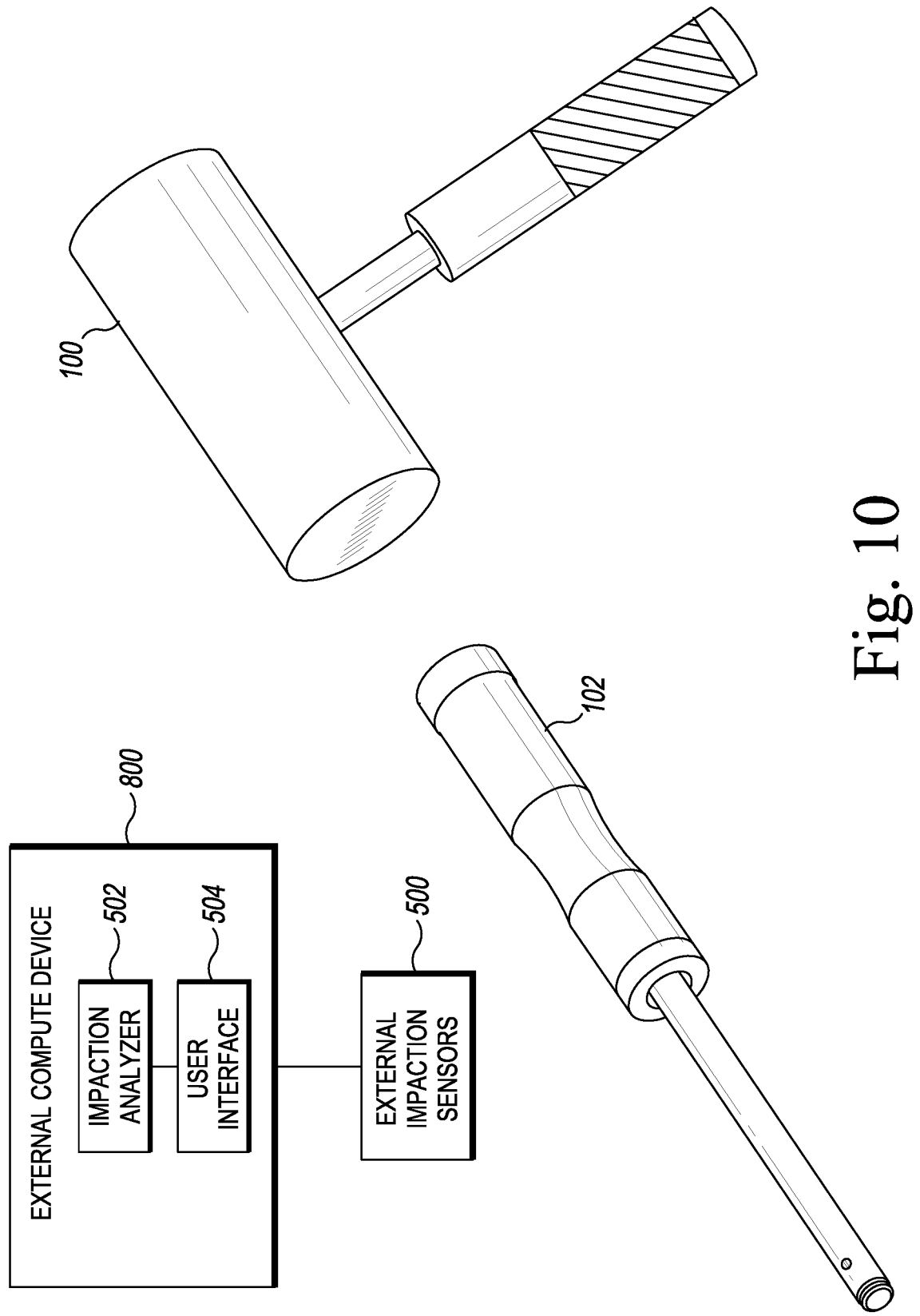
FIG. 10 is a schematic drawing of another embodiment of a system for determining whether an orthopaedic implant is sufficiently seated in a bone of a patient including an orthopaedic mallet, an orthopaedic surgical tool, and an external compute device including the impaction analyzer of FIG. 5.
Figure 11:
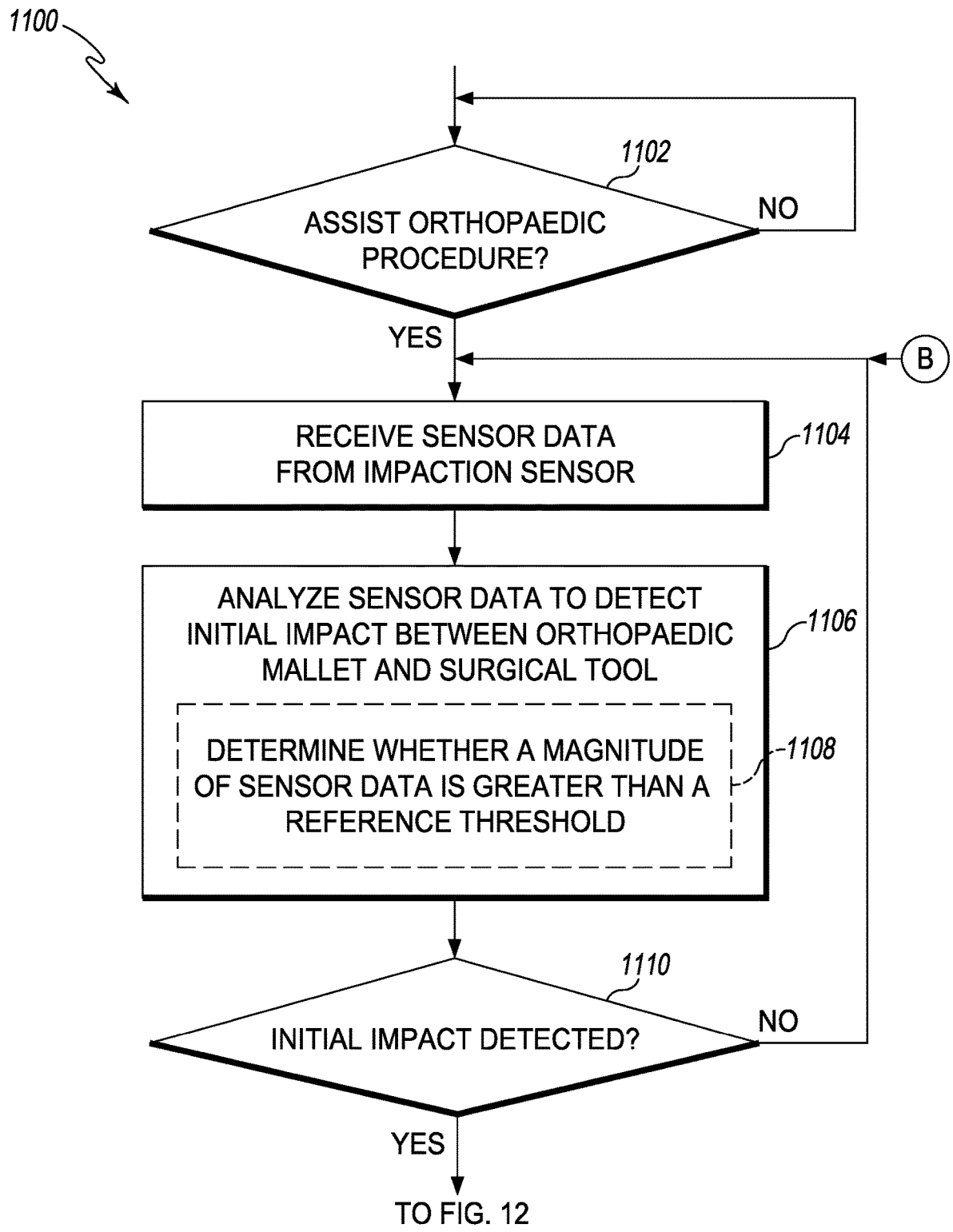
FIGS. 11-14 is a flowchart of a method for determining whether an orthopaedic implant is sufficiently seated in a bone of a patient during an orthopaedic surgical procedure, which may be executed by an impaction analyzer.

Referring now to FIGS. 8-10, in some embodiments, the impaction sensors 500, the impaction analyzer 502, and/or the user interface 504 may be distributed across different devices. For example, as shown in FIG. 8, the impaction sensor(s) 500 may be located on the orthopaedic mallet 100, while the impaction analyzer 502 is included in an external compute device 800. In such embodiments, the orthopaedic mallet 100 may also include the user interface 504, or the user interface 504 may be included in the external compute device 800 (or in both the orthopaedic mallet 100 and the external compute device 800).

In use, the orthopaedic mallet 100 is configured to transmit the sensor data produced or generated by the impaction sensor(s) 500 to the external compute device 800 for analysis by the impaction analyzer 502. To do so, the orthopaedic mallet 100 illustratively includes a communication circuit 802 configured to communicate with a corresponding communication circuit 804 of the external compute device 800. The communication circuits 802, 804 may be embodied as any type of communication circuits or devices capable of facilitating communications between the orthopaedic mallet 100 and the external compute device 800. To do so, the communication circuits 802, 804 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The external compute device 800 may be embodied as any type of compute device capable of performing the functions of the impaction analyzer 502, such as a desktop computer, a special-built compute device, a mobile compute device, a laptop computer, a tablet computer, or other computer or compute device. In addition to the impaction analyzer 502, the communication circuit 804, and, optionally, the user interface 504, the external compute device 800 may include other components commonly found in a compute device, such as a data storage device and various input devices (e.g., a keyboard, mouse, etc.)

As discussed above, the external compute device 800 is configured to receive the impaction sensor data from the orthopaedic mallet 100, and the impaction analyzer 502 of the external compute device 800 is configured to analyze the received sensor data to determine whether the orthopaedic implant 104 is sufficiently seated as discussed above. In embodiments in which the external compute device 800 includes the user interface 504, the impaction analyzer 502 may be further configured to control the user interface 504 (e.g., a display) to generate an alert or notification to the orthopaedic surgeon related to the seating of the orthopaedic implant 104 as discussed above. In those embodiments in which the external compute device 800 does not include the user interface 504, the external compute device 800 may be configured to transmit the alert or notification back to the orthopaedic mallet 100 for display or output to the orthopaedic surgeon on the user interface 504 of the orthopaedic mallet 100.

In other embodiments, as shown in FIG. 9, the impaction sensor(s) 500 may be located on the surgical tool 102, and the impaction analyzer 502 and the user interface 504 may be located on the orthopaedic mallet 100. In such embodiments, the surgical tool 102 also includes a communication circuit 906, which may be substantially similar to the communication circuits 802, 804 described above. In use, the surgical tool 102 is configured to transmit the impaction sensor data sensed, generated, or otherwise produced by the impaction sensor(s) 500 to the orthopaedic mallet 100 for analysis by the impaction analyzer 502 as described above.

Alternatively, the impaction analyzer 502 and the user interface 504 may be located in the external compute device 800, rather than the orthopaedic mallet 100. In such embodiments, the surgical tool 102 is configured to transmit the impaction sensor data to the external compute device 800 for analysis by the impaction analyzer 502 as described above. The external compute device 800 may subsequently provide any alert or notification generated by the impaction analyzer 502 to the orthopaedic surgeon via the user interface 504 located on the external compute device 800 (or on orthopaedic mallet 100, depending on the particular embodiment).

In some embodiments, as shown in FIG. 10, the impaction sensor(s) 500 may be embodied as external impaction sensor(s), which are not located on either the orthopaedic mallet 100 or the surgical tool 102. Furthermore, in such embodiments, the impaction analyzer 502 and the user interface 504 may be located on the external compute device 800. As such, the orthopaedic mallet 100 and the surgical tool 102 may be embodied as typical orthopaedic tools (i.e., not "smart" surgical tools) and include no electrical components.

In such embodiments, the external impaction sensor(s) 500 may be embodied any type of sensor capable of producing sensor data indicative of impaction between the orthopaedic mallet 100 and the surgical tool 102, even though the sensors 500 are not in physical contact with either the orthopaedic mallet 100 or the surgical tool 102. For example, in an embodiment, the external impaction sensor(s) 500 are embodied as audio sensors (e.g., microphones) capable of generating audio sensor data indicative of impaction between the orthopaedic mallet 100 and the surgical tool 102. In such embodiments, the audio sensor data may resemble the sensor data illustrated in FIGS. 2-4 and, as such, the impaction analyzer 502 may determine whether the orthopaedic implant 104 is sufficiently seated by analyzing the audio sensor data as described above. For example, the impaction analyzer 502 may analyze the audio sensor data to identify the initial and secondary impacts, determine the temporal length between the initial and secondary impacts, and determine whether the orthopaedic implant 104 is sufficiently seated based on the temporal length (or on a difference between temporal lengths of sequential impactions).

Referring now to FIGS. 11-14, in use, the impaction analyzer 502 may perform a method 1100 for determining whether an orthopaedic implant is sufficiently seated. The method 1100 begins with block 1102 in which the impaction analyzer 502 determines whether to assist the orthopaedic surgeon in the performance of an orthopaedic surgical procedure. For example, in block 1102, the impaction analyzer 502 may determine whether the orthopaedic mallet 100 (or external compute device 800) has been switched on and/or whether a proper input button or other device (e.g., a "start" button) has been selected by the orthopaedic surgeon. If so, the method 1100 advances to block 1104 in which the impaction analyzer 502 receives the sensor data from the impaction sensor(s) 500.

Subsequently, in block 1106, the impaction analyzer 502 analyzes the sensor data to detect or identify the initial impact 202 of an impaction. To do so, in block 1108, the impaction analyzer 502 may determine whether a magnitude of the sensor data (e.g., a magnitude of force) is greater than a reference threshold. That is, the impaction analyzer 502 may determine that an initial impact of the orthopaedic mallet 100 and the surgical tool 102 (or other structure) has occurred in response to a determination that a peak of the sensor data is greater than a reference threshold force or other measurement. In block 1110, if the impaction analyzer 502 determines that no initial impact has been detected, the method 1100 loops back to block 1104 in which the impaction analyzer 502 receives addition sensor data from the impaction sensor 500. In this way, the impaction analyzer 502 is configured to sample the sensor data. It should be appreciated that the sampling rate of the impaction analyzer 502 must be sufficiently high enough to detect the initial and secondary impacts. Illustratively, the impaction analyzer 502 may utilize a sampling rate of 100 kilohertz (kHz), but other sampling rates may be used in other embodiments.

Figure 12:
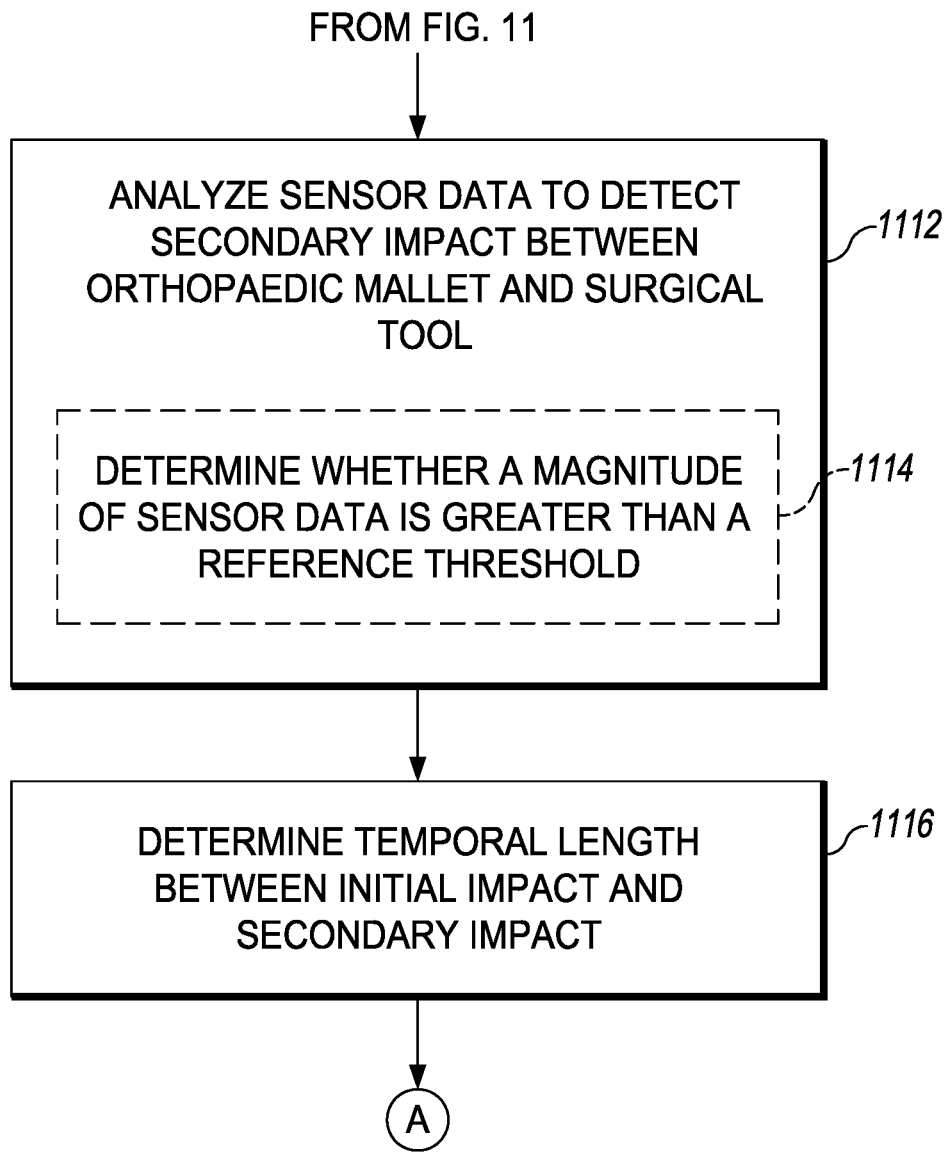
Figure 13:
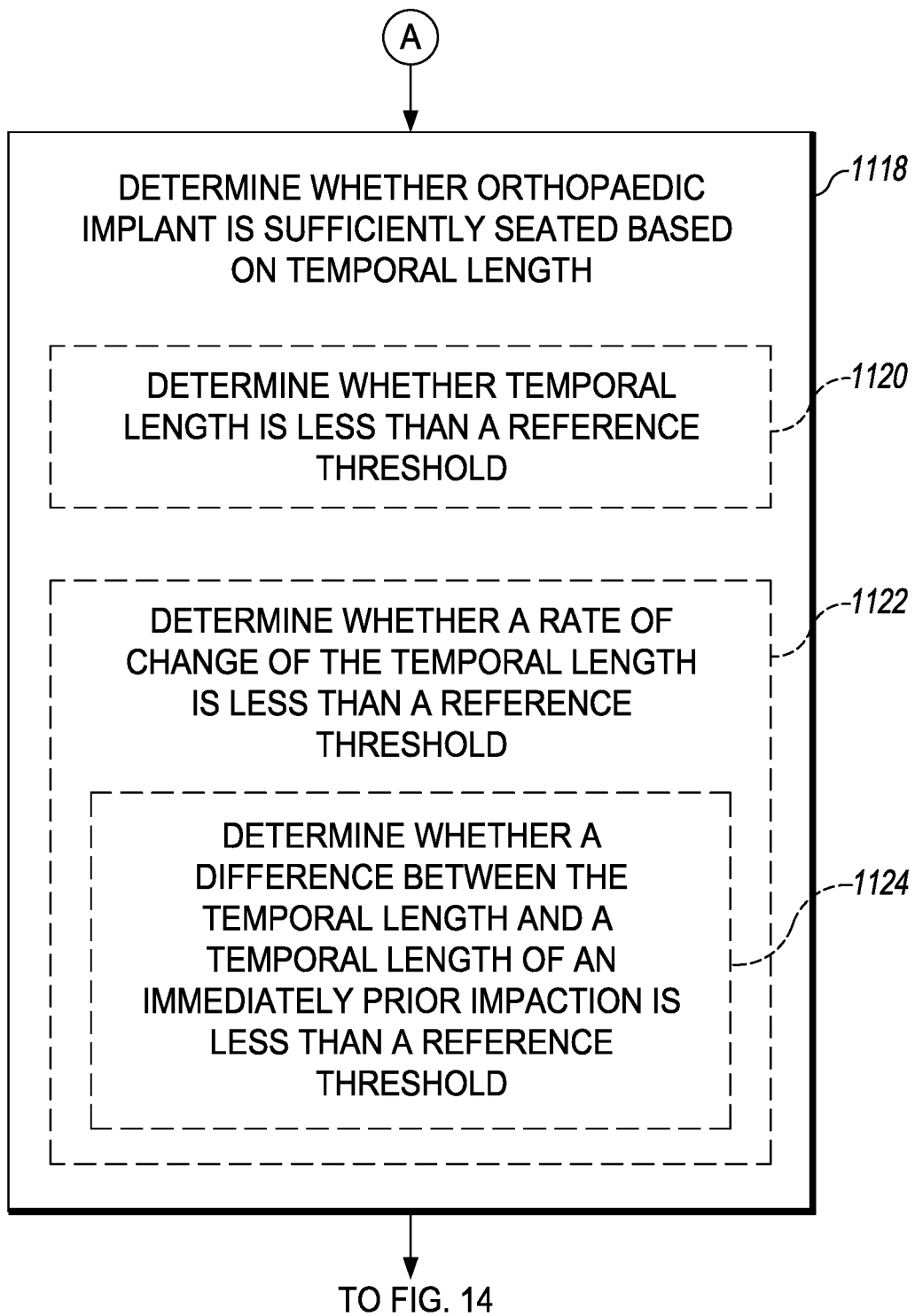

If, however, the impaction analyzer 502 detects the initial impact of the impaction between the orthopaedic mallet 100 and the surgical tool 102, the method 1100 advances to block 1112 of FIG. 12. In block 1112, the impaction analyzer 502 analyzes the sensor data to detect or identify the secondary impact 204 of an impaction. To do so, in block 1114, the impaction analyzer 502 may determine whether a magnitude of the sensor data is greater than a reference threshold, which may be different (e.g., lower) than the reference threshold used to detect the initial impact.

After the impaction analyzer 502 has detected the initial and secondary impacts 202, 204, the impaction analyzer 502 determines or calculates the temporal length 210 between the initial impact 202 and the secondary impact 204 in block 1116. Subsequently, in block 1118 of FIG. 13, the impaction analyzer 502 determines whether the orthopaedic implant 104 is sufficiently seated in the patient's bone 106 based on the determined temporal length. To do so, in some embodiment as discussed above, the impaction analyzer 502 may determine whether the calculated temporal length is less than a reference threshold in block 1120. Alternatively, in block 1122, the impaction analyzer 502 may determine whether a rate of change of the temporal lengths of sequential impactions between the orthopaedic mallet 100 and the surgical tool 102 is less than a reference threshold. For example, as shown in block 1124, the impaction analyzer 502 may determine whether a difference between the temporal length of the most recent impaction and temporal length of the immediately prior impactions is less than a reference threshold as discussed above in regard to FIGS. 3 and 4.

Figure 14:
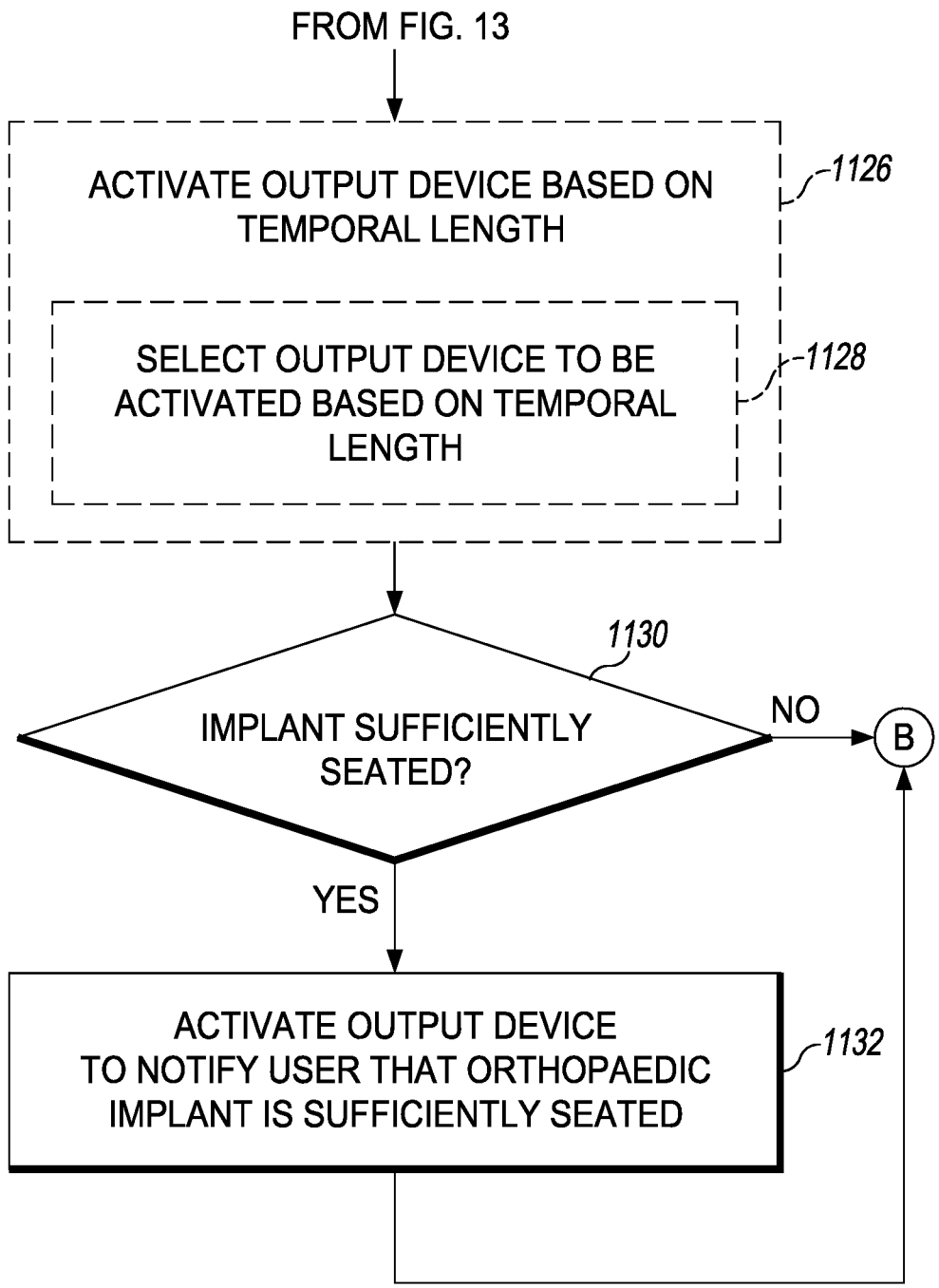

In some embodiments, in block 1126 of FIG. 14, the impaction analyzer 502 is configured to activate one or more output devices based on the determined temporal length. To do so, in block 1128, the impaction analyzer 502 may select the output device to be activated. For example, in some embodiments as discussed above, the impaction analyzer 502 may be configured to active different output devices (e.g., different LEDs) based on whether the determined temporal length (or difference of temporal lengths) is greater than a first referenced threshold indicative that the orthopaedic implant 104 is not sufficiently seated, less than the first reference threshold but greater than a second reference threshold indicative that the orthopaedic implant 104 is sufficiently seated (but not overly impacted), or is less than the second reference threshold indicative that the orthopaedic implant 104 is overly impacted and additional impacting may result in the fracturing of the patient's bone.

Regardless, in block 1130, the impaction analyzer 502 determines whether the orthopaedic implant 104 is sufficiently seated based on the determined temporal length(s) as discussed above. If not, the method 1100 loops back to block 1104 in which the impaction analyzer 502 receives and analyzes further sensor data. If, however, the impaction analyzer 502 determines that the orthopaedic implant 104 is properly seated based on the determined temporal length(s), as discussed above, the method advances to block 1132 in which the impaction analyzer 502 actives the appropriate output device 520 to notify the orthopaedic surgeon or other user that the orthopaedic implant 104 is sufficiently seated (e.g., by illuminating an LED or displaying a message on a display screen).

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. One or more non-transitory, machine-readable media comprising a plurality of instructions that, in response to execution, cause one or more processors to:
    obtain, from an impaction sensor, sensor data indicative of an impaction of an orthopaedic mallet and a surgical tool, wherein the impaction comprises an initial impact between the orthopaedic mallet and the surgical tool and a secondary impact between the orthopaedic mallet and the surgical tool that occurs subsequent to the initial impact;
    analyze the sensor data to detect the initial impact and the secondary impact;
    determine a temporal length between the initial impact and the secondary impact; and
    determine whether the orthopaedic implant is sufficiently seated into the bone based on the temporal length.

2. The one or more non-transitory, machine-readable media of claim 1, wherein to determine whether the orthopaedic implant is sufficiently seated into the bone comprises to determine that the orthopaedic implant is sufficiently seated in response to a determination that the temporal length between the initial impact and the secondary impact is less than a reference threshold.

3. The one or more non-transitory, machine-readable media of claim 1, wherein to determine whether the orthopaedic implant is sufficiently seated into the bone comprises to determine that the orthopaedic implant is sufficiently seated in response to a determination that a difference between the temporal length and a prior temporal length of a prior initial impact and a corresponding prior secondary impact is less than a reference threshold.

4. The one or more non-transitory, machine-readable media of claim 1, wherein the impaction comprises a second impaction and the temporal length comprises a second temporal length,
    wherein the plurality of instructions, in response to execution, further cause the one or more processors to:
    obtain, from the impaction sensor, additional sensor data indicative of a first impaction of the orthopaedic mallet and the surgical tool that occurred prior to the second impaction, wherein the first impaction comprises an initial impact between the orthopaedic mallet and the surgical tool and a secondary impact between the orthopaedic mallet and the surgical tool that occurs subsequent to the initial impact of the first impaction,
    analyze the additional sensor data to detect the initial impact of the first impaction and the secondary impact of the first impaction,
    determine a first temporal length between the initial impact of the first impaction and the secondary impact of the first impaction, and
    determine that the orthopaedic implant is sufficiently seated in response to a determination that a difference between the first temporal length and the second temporal length is less than a referenced amount.

5. The one or more non-transitory, machine-readable media of claim 1, wherein to detect the initial impact and the secondary impact comprises to determine that a value of the sensor data is greater than a reference threshold.

6. The one or more non-transitory, machine-readable media of claim 1, wherein the plurality of instructions, in response to execution, further cause one or more processors to activate an output device of the orthopaedic mallet in response to a determination that the orthopaedic implant is sufficiently seated into the bone to alert a user of the orthopaedic mallet.

7. The one or more non-transitory, machine-readable media of claim 6, wherein to activate the output device of the orthopaedic mallet comprises to determine which one of a plurality of output devices of the orthopaedic mallet to activate as a function of the temporal length.

8. The one or more non-transitory, machine-readable media of claim 6, wherein to activate the output device comprises to activate a visual output device, an audible output device, or a tactile output device of the orthopaedic mallet.

9. The one or more non-transitory, machine-readable media of claim 1, wherein to obtain the sensor data indicative of the impaction of the orthopaedic mallet and the surgical tool comprises to obtain sensor data from a force sensor, a strain gauge, or an audio sensor.

10. The one or more non-transitory, machine-readable media of claim 1, wherein to obtain sensor data comprises to obtain, from an impaction sensor located on the orthopaedic mallet, sensor data indicative of the impaction of the orthopaedic mallet and the surgical tool.

11. The one or more non-transitory, machine-readable media of claim 1, wherein to obtain sensor data comprises to obtain, from an impaction sensor located on the surgical tool, sensor data indicative of the impaction of the orthopaedic mallet and the surgical tool.

12. The one or more non-transitory, machine-readable media of claim 1, wherein to obtain sensor data comprises to obtain, from an impaction sensor separate from the orthopaedic mallet and from the surgical tool, sensor data indicative of the impaction of the orthopaedic mallet and the surgical tool.

* * * * *